United States Patent [19]

Hassler et al.

[11] Patent Number: 4,526,168

[45] Date of Patent: Jul. 2, 1985

[54] APPARATUS FOR DESTROYING CALCULI IN BODY CAVITIES

[75] Inventors: Dieter Hassler; Heinz Kresse, both of Uttenreuth; Helmut Reichenberger, Eckental; Georg Naser, Zirndorf, all of Fed. Rep. of Germany

[73] Assignee: Siemens Aktiengesellschaft, Berlin & Munich, Fed. Rep. of Germany

[21] Appl. No.: 371,924

[22] Filed: Apr. 26, 1982

[30] Foreign Application Priority Data

May 14, 1981 [DE] Fed. Rep. of Germany ....... 3119295

[51] Int. Cl.³ .............................................. A61B 17/22
[52] U.S. Cl. ............................. 128/303 R; 128/24 A; 128/328
[58] Field of Search ................ 128/328, 24 A, 303 R, 128/419 R, 660

[56] References Cited

U.S. PATENT DOCUMENTS

| | | |
|---|---|---|
| 3,237,623 | 3/1966 | Gordon . |
| 3,958,559 | 5/1976 | Glenn et al. ................. 128/24 A X |
| 4,311,147 | 1/1982 | Hausler ................................ 128/328 |
| 4,315,514 | 2/1982 | Drewes et al. ................... 128/24 A |

FOREIGN PATENT DOCUMENTS

| | | |
|---|---|---|
| 2053982 | 5/1972 | Fed. Rep. of Germany . |
| 2202989 | 7/1973 | Fed. Rep. of Germany . |
| 2223319 | 7/1975 | Fed. Rep. of Germany . |
| 2351247 | 10/1975 | Fed. Rep. of Germany . |
| 2645738 | 4/1977 | Fed. Rep. of Germany . |
| 2722252 | 4/1979 | Fed. Rep. of Germany . |
| 602180 | 4/1978 | U.S.S.R. ............................. 128/328 |

*Primary Examiner*—Lee S. Cohen
*Attorney, Agent, or Firm*—Hill, Van Santen, Steadman & Simpson

[57] ABSTRACT

In exemplary embodiments, an ultrasonic transducer serves as vibration generator. It is an object of the disclosure to construct such an apparatus which, with the simplest technical construction, is functionally reliable and can be operated in a very adaptable manner and which is simultaneously especially productive with regard to the desired destruction effect. In accordance with the disclosure this object is achieved in that an ultrasonic transducer to be focused on the calculus serves as a direct acoustic irradiator for the calculus, which irradiator has a surface area such that the sound energy per square unit along the transmission path is sufficiently small so as to avoid tissue damage on the one hand, but is sufficiently great at the focus point that is suffices for the destruction of the calculus disposed at the focus, on the other hand.

12 Claims, 9 Drawing Figures

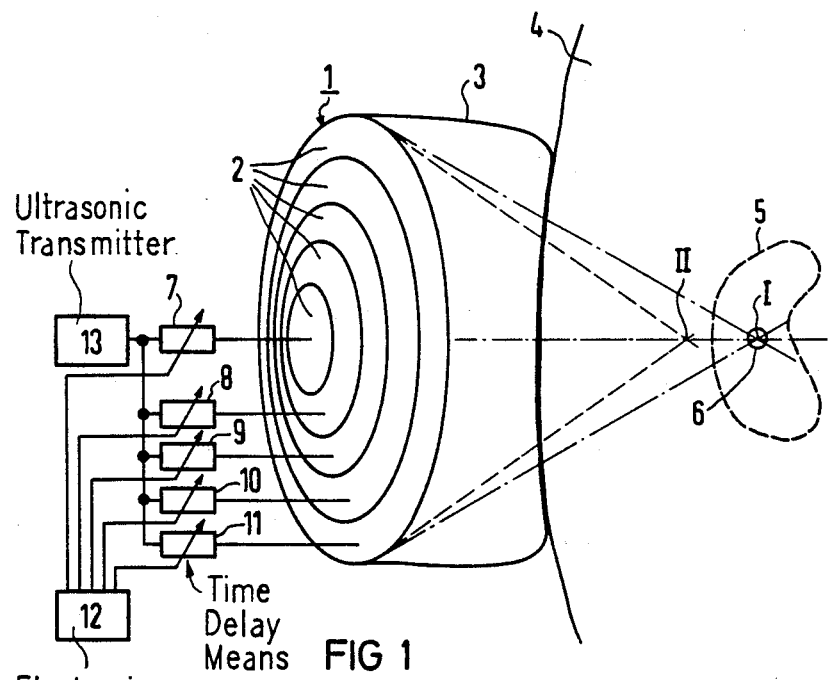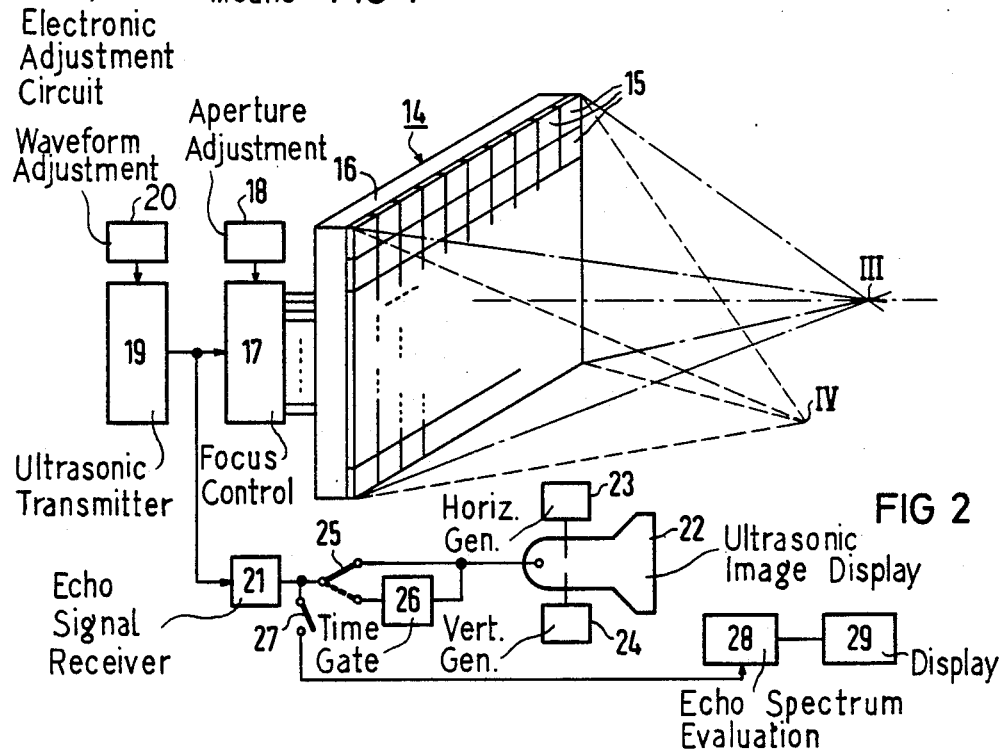

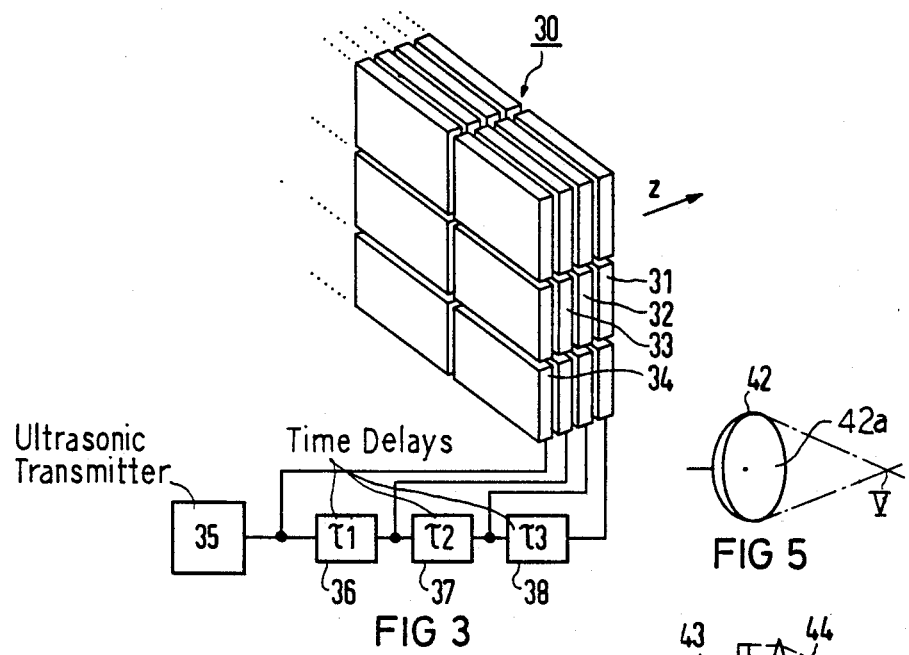
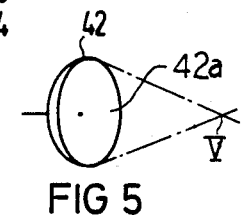
FIG 5
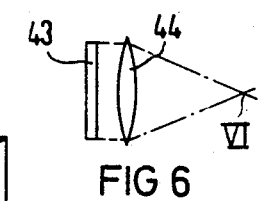
FIG 6
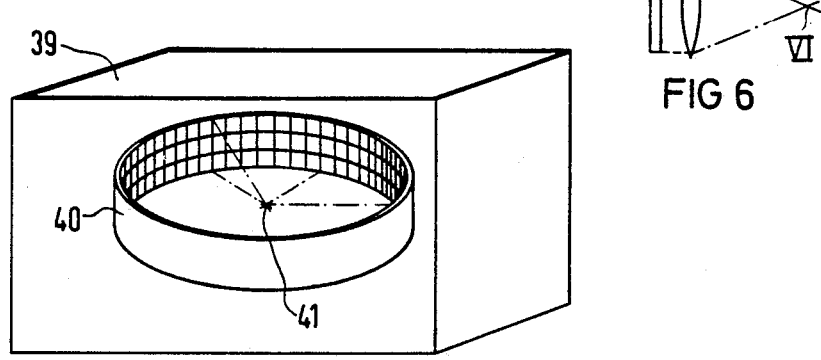
FIG 4
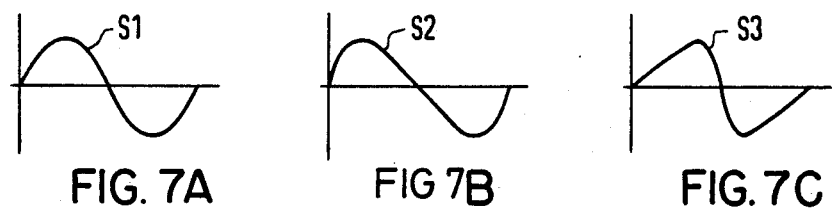
FIG. 7A      FIG 7B      FIG. 7C

APPARATUS FOR DESTROYING CALCULI IN BODY CAVITIES

BACKGROUND OF THE INVENTION

The invention relates to an apparatus for destroying calculi in body cavities with the aid of an ultrasonic transducer as vibration generator.

From German OS No. 20 53 982, an apparatus for destroying stones in the urinary bladder, in the ureter, in the kidney, and the like, is already known, in which the sonic energy of an ultrasonic transducer is employed in order to set a work attachment at the tip of a probe into longitudinal vibrations. The work attachment then breaks up the stone. Such an apparatus, however, is technically quite complicated; it is semi-invasive and also not very accurate in aiming in application. From U.S. Pat. No. 3,237,623, in conjunction with the destruction of cells of a cell group in the eye or brain, yet another apparatus, which operates with an ultrasonic transducer as excitation vibrator, is known. In the case of this apparatus, however, with the aid of the ultrasound, punctiform fields of higher temperature are produced by means of which then the respective cell group is destroyed. In the case of apparatus of this type, the energy density is too low to be able to destroy calculi such as stone, or the like. The above-cited apparatus which operate with ultrasound are thus poorly suited for destroying calculi specifically in body cavities. For this reason, in practice, up to the present time only such apparatus have been employed which do not function on the basis of ultrasonic excitation. These apparatus relate to shock wave generators with a focusing chamber wherein at the focal point of a water-filled revolution ellipsoid there is disposed a spark discharge path which, in the case of electric ignition through spark discharge, generates a shock wave. The shock wave is transmitted via a coupling membrane to the body of the patient; it thus reaches the calculus which, due to a corresponding previous adjustment of the focusing chamber, is disposed at the second focal spot of the revolution ellipsoid. Apparatus of this type are, for example, prior-known from German Pat. No. 22 23 319 and German Pat. No. 23 51 247. Spark discharges require high sparking voltages in the range of between 15 to 30 kV. However, these high sparking voltages raise problems regarding a satisfactory insulation with respect to the patient. Moreover, spark discharges always lead to burning loss. This requires constant maintenance, and the number as well as frequency of ignitions (which are necessary for a treatment) is limited.

SUMMARY OF THE INVENTION

It is the object of the present invention to provide an apparatus for destroying calculi which, with the simplest technical construction, is functionally reliable and can be very readily adapted to different treatment situations and which is simultaneously particularly productive with regard to the desired destruction effect.

With an apparatus of the type initially cited, the object is achieved in accordance with the invention in that an ultrasonic transducer, to be focused on the calculus, serves as direct acoustic irradiator for the calculus, the unit being of such surface area that the sound energy per square unit (or sound intensity) along the transmission path is small enough to avoid tissue damage, on the one hand, but is sufficiently great at the focus point so that calculus at the region of such focus is effectively destroyed, on the other hand.

In accordance with the invention, the shock wave for the calculus is now directly generated by a focusing ultrasonic transducer. This ultrasonic transducer has such a large surface area that a sound energy per square unit results at the focus which reliably destroys the calculus, but which causes no tissue damage along other body tissue. An ultrasonic transducer of this type as direct acoustic irradiator is technically very simply constructed; it is functionally reliable and can also be adapted in a very versatile manner. Moreover, an ultrasonic transducer can be well encapsulated in terms of insulation. Problems regarding insulation thus do not occur even when the ultrasonic transducer is immersed in a water bath for coupling to a patient. A particularly expedient utilization of the ultrasonic transducer results if the latter is also simultaneously designed for the recording of real time-images, for example, by means of B-image or C-image scanning. In such an instance, then, e.g. on the basis of the real time-image, the most favorable irradiation (or beaming) angle for the shock wave in the direction of the calculus can be ascertained. In addition, on the basis of such a real time-image, it is also possible to ascertain to what extent the shock application has led to success. For this purpose, merely a corresponding splitter-echo image need be evaluated. Of course, instead of the B-image evaluation, or together with the latter, an additional evaluation by means of a spectral analysis can be carried out. For this purpose, there is then associated with the ultrasonic transducer a separate evaluation device which examines the echoes occurring after a shock wave as to their spectral composition. From the evaluation result conclusions can then again be drawn regarding the success of the shock application. In a preferred embodiment, however, it is also possible to associate with the ultrasonic transducer a device for changing the aperture of the radiation surface and a device for checking the acoustic path from the ultrasonic transducer to the calculus. Through change of the aperture the diameter of the acoustic path can be narrowed. Body regions, such as e.g. the ribs or the like, which could be additionally endangered by the shock wave, can thus by blocked out. The shock wave then traverses only such regions in the direction of the calculus which are not exposed to any additional danger. In case it is desired and expedient, for the purpose of pre-abortion of a calculus, it is also possible to additionally associate an x-ray installation with the apparatus for destroying calculus. However, the calculus can also be located with the aid of an ultrasonic location system which is associated with the apparatus, or the ultrasonic transducer of the apparatus can itself form a part of such a location system. Additional systems of this type for locating a calculus are already prior-known from German Pat. No. 27 22 252.

Further advantages and details of the invention are apparent from the following description of an exemplary embodiment on the basis of the accompanying drawing sheets in conjunction with the subclaims; and other objects, features and advantages will be apparent from this detailed disclosure and from the appended claims.

BRIEF DESCRIPTION OF THE DRAWINGS

FIG. 1 illustrates a first exemplary embodiment of the invention comprising a focusing ultrasonic transducer, consisting of concentric rings;

FIG. 2 illustrates a second exemplary embodiment of the invention comprising a focusing surface-ultrasonic array as the ultrasonic transducer, which contains a plurality of individual transducer elements in a matrix-type arrangement;

FIG. 3 illustrates a modification of the exemplary embodiment of FIG. 2;

FIG. 4 illustrates a fourth exemplary embodiment of the invention comprising a belt arrangement of an ultrasonic array and coupling via a water bath;

FIGS. 5 and 6 illustrate two additional exemplary embodiments utlizing mechanically focusing ultrasonic transducers; and FIG. 7 comprising FIGS. 7A, 7B and 7C illustrates three diagrams showing possible signal shapes for the generation of shock formation at varying distances relative to the transducer surface.

DETAILED DESCRIPTION

In FIG. 1, a focusing ultrasonic transducer 1, which exhibits a plurality of ultrasonic transducers 2 in concentric annular arrangement, is coupled via a water-filled bag 3 with the body surface 4; for example, on the back, at the height of a kidney 5 of a patient. The kidney 5 contains, as is schematically indicated, a calculus 6 in the form of a kidney stone. The ultrasonic transducer 1 with an annular structure of the transducer elements 2 is mechanically and electronically focused such as e.g. described in German OS No. 22 02 989. Accordingly, it comprises a number of delay devices 7 through 11, corresponding to the number of rings, which devices are adjustable, by means of an electronic adjustment circuit 12, to different delay times. Through adjustment of different delay times, the distance of the focus of the ultrasonic transducer from its radiation surface can be varied. Thus, through corresponding adjustment of the delay times of the delay devices, the focus can be displaced (or shifted), until it is disposed at the location of the calculus 6 within the kidney 5. In FIG. 1 this location of the focus is indicated with reference character I. An additional location of the position of a focus is indicated at II outside the kidney so as to indicate that circuit 12 provides for a substantial range of focusing adjustment. Serving the purpose of generating shock waves after adjustment of the correct focus is a corresponding ultrasonic transmitter 13. In a modification of the arrangement, the delay devices can be replaced by a corresponding number of triggerable pulse transmitters which are activated at different times.

In FIG. 2, the focusing ultrasonic transducer is an ultrasonic array 14 which is comprised of a plurality of individual transducer elements 15 which are secured in mosaic-fashion on a support part 16. The ultrasonic array is electronically focused in such a manner that not only the distance of the focus from the radiation surface of the array can be altered, but, additionally also for carrying out beam pivoting, the angle of the connection straight lines to the focus can be altered. Ultrasonic arrays which are capable of being focused in such a fashion are e.g. prior-known from German OS No. 26 45 738. In the exemplary embodiment of FIG. 2, the possibility of selectively focusing at different angles and distances is indicated through representation of two focus points III and IV. The device for adjustment of different delay times, which also simultaneously comprises the activation switches for the individual transducer elements 15 of the array 14, bears the reference numeral 17 in FIG. 2. Additionally also associated with this device 17 is a device 18 for altering the aperture of the radiation surface of the ultrasonic array 14. Reference number 19 designates the transmitter generator with which, in turn, a device 20 for the adjustment of different signal waveforms is associated.

In addition, there is also associated with the shock wave generator of FIG. 2 a conventional device for recording real time-images, for example, a B-image or C-image display; in particular, a sector image may be recorded utilizing the entire transducer aperture as an active scanning surface. This device comprises an echo signal receiver 21, whose output signals are supplied to a picture tube 22 with a horizontal time-base generator 23 and a vertical time-base generator 24 for the purpose of recording in the form of a real time-image. In switching-over a switch 25 to the switching position illustrated in broken lines a time gate 26 is connected into the signal path between the echo signal receiver 21 and the picture tube 22. With the aid of this time gate 26, then, e.g. C-images can be represented. By means of switch 27 also an evaluation device 28 can be switched on at the output of the echo signal amplifier 21, which evaluation device 28 evaluates the arriving echo signals in such a fashion that it ascertains the success of a destruction action through analysis of the arriving echo spectrum. The result is displayed on a display device 29. By means of the real time-image the position of the calculus in relation to the ultrasonic transducer can be reliably determined. The correct irradiation angle for the shock wave thus results. For the purpose of locating, however, additionally also an x-ray installation or a separate ultrasonic locating system can be employed, whereby, in the latter instance, the ultrasonic transducer 14 itself can be part of this locating system. On the viewing screen of the picture tube 22, however, the success of a shock execution can also be checked (or monitored) on the basis of a splitter echo image resulting e.g. in the case of breaking up of the calculus. This checking (or monitoring) can proceed in addition to that of the device 28. With the device 18 the aperture of the radiation surface of the ultrasonic transducer 14 can be altered. As initially already indicated, the transit path of the shock waves through the body tissue of the patient can hereby be narrowed down or restricted to body regions which are not endangered by the shock wave. It is to be understood that all additional devices, described on the basis of FIG. 2, for construction of a real time-image, conducting a spectral analysis, and/or also for altering the aperture, are applicable to any other inventively employed ultrasonic transducer, in particular, such as are illustrated in FIGS. 1 and 3 through 6.

The ultrasonic array of FIG. 2, for the purpose of attaining high pulse peak power with a simultaneously low exciting voltage of the transducers, can be comprised of several individual transducers layered in series (or in tandem) which are chronologically successively activatable in such a manner that, in the radiation direction, an energy adding-up of the partial energies of the individual transducers takes place. Such an embodiment with tandemly arranged (in line) individual transducer layers is illustrated in FIG. 3. Reference number 30 designates the layered ultrasonic array; the transducer layers themselves bear the identity numerals 31 through 34. Serving the purpose of the chronologically correct, delayed activation of the individual layers is a transmitting generator 35 with delay devices 36, 37 and 38, which have the delay times $\tau 1$, $\tau 2$ and $\tau 3$. The radiation direction of the array is indicated with z.

FIG. 4 illustrates a further embodiment for applications in a water bath 39, for example a medical bath. The ultrasonic transducer 40 has the shape of a belt. This belt lies in the water bath with an internally-directed radiation surface of transducer elements, arranged in mosaic-fashion, for encircling the body of the patient. The position is so adjusted that the focus 41 of the transducer 40 is disposed at the location of the calculus to be destroyed in the body of the patient.

FIG. 5 illustrates an ultrasonic transducer 42 which is purely mechanically focused through mechanical fashioning of the contour of its radiating surface 42a so as to have a focal point at V.

FIG. 6 illustrates an ultrasonic transducer 43 which is planar per se and with which a lens 44 for the purpose of focusing is arranged so as to focus the transmitted ultrasonic energy on a focal point VI.

FIG. 7 illustrates different excitation waveforms for a focusing ultrasonic transducer according to the invention. The excitation shape S1 of FIG. 7A has the normally conventional sinusoidal shape. However, for the purpose of variation of the distance of the shock formation from the transducer surface, transmission should be carried out with a signal shape as a function of time differing from the sinusoidal shape S1. Such possible signal shapes are indicated in FIGS. 7B and 7C by signals S2 and S3.

In all the illustrated embodiments the focusing ultrasonic transducers have a radiation surface area which lies in the range of at least five times the surface area of a conventional ultrasonic transducer for ultrasonic therapy. The surface area of conventional ultrasonic transducers for ultrasonic therapy amounts to approximately 20 cm$^2$. A focusing ultrasonic transducer according to the invention thus should exhibit a radiation surface area which amounts to at least 100 cm$^2$. The pulse peak power of such a focusing ultrasonic transducer expediently lies at least in the range of 100 kW. Distributed over the above cited radiation surface area, a sound energy per square unit of 1 kW/cm$^2$ results. In the case of a dimensioning of this type, calculi are destroyed, whereas on the transmission path no danger to other tissue is provided. The inventive apparatus can possibly also be employed in the case of combating cancer.

It will be apparent that many modifications and variations may be made without departing from the scope of the teachings and concepts of the present invention.

We claim as our invention:

1. Apparatus for destroying concrements in a body cavity, comprising
   (a) an ultrasonic transducer for generating ultrasonic energy pulses, each ultrasonic energy pulse transforming to a shock wave during propagation,
   (b) means for exciting said ultrasonic transducer to generate ultrasonic energy pulses with each pulse having a pulse peak power of at least one hundred kilowatts,
   (c) means for electrically focusing said ultrasonic energy pulses to a focal zone,
   said ultrasonic transducer having an emission surface area which is greater than 100 cm$^2$,
   said ultrasonic transducer emitting in operation said ultrasonic energy pulses, each pulse having a pulse peak power of at least one hundred kilowatts distributed over said surface area, such that the ultrasonic energy per square unit along the transmission path is sufficiently small so as to avoid tissue damage, on the one hand, but is sufficiently large at said focal zone that it suffices for destroying the concrement disposed in the region of said focal zone, on the other hand,
   wherein said ultrasonic transducer comprises a plurality of piezoelectric transducer elements, and wherein said means for electrically focusing comprises electronic circuit means for triggering said piezoelectric transducer elements in a predetermined time sequence at different times.

2. Apparatus according to claim 1, wherein said transducer elements are arranged in matrix form.

3. Apparatus according to claim 1, further comprising means for effecting an electronic displacement of said focal zone.

4. Apparatus according to claim 1, wherein a liquid receiving bag is connected with the ultrasonic transducer, said liquid bag being filled with a liquid.

5. Apparatus according to claim 1, wherein a water bath is coupled to said ultrasonic transducer.

6. Apparatus according to claim 1, characterized in that, for attaining high pulse peak power with a simultaneously low exciting voltage, the ultrasonic transducer comprises several tandemly arranged individual transducer layers which are chronologically successively activatable such that in the radiation direction an energy adding-up of the partial energies of the individual transducer layers takes place.

7. Apparatus according to claim 1, with said ultrasonic transducer emitting each of said ultrasonic energy pulses with a predetermined signal shape which differs from a sinusoidal shape, so that said shock wave is formed at a respectively predetermined distance relative to the transducer surface.

8. Apparatus according to claim 1, wherein said ultrasonic transducer also comprises means for receiving echo signals for the recording of real-time images.

9. Apparatus according to claim 1, further comprising an echo signal receiver and an evaluation device connected to the ultrasonic transducer, the echo signal receiver receiving echo signals which originate from said ultrasonic energy pulses, and supplying its output to the evaluation device for evaluation in such a manner that the success of a destruction action in said concrement is ascertained.

10. Apparatus according to claim 1, further comprising means for changing the aperture of the emission surface area of said ultrasonic transducer, and means for monitoring the acoustic path from the ultrasonic transducer to said concrement.

11. Apparatus according to claim 1, further comprising an x-ray installation means for locating a concrement.

12. Apparatus according to claim 1, further comprising an ultrasonic locating means for locating a concrement.

* * * * *